(12) United States Patent
Luzon

(10) Patent No.: US 8,636,747 B2
(45) Date of Patent: Jan. 28, 2014

(54) DERMABRASION DEVICES AND SYSTEMS

(75) Inventor: Josef Luzon, Jersey City, NJ (US)

(73) Assignee: Derma Dream Group Ltd., Tortola (VG)

( * ) Notice: Subject to any disclaimer, the term of this patent is extended or adjusted under 35 U.S.C. 154(b) by 1084 days.

(21) Appl. No.: 11/958,771

(22) Filed: Dec. 18, 2007

(65) Prior Publication Data

US 2008/0213321 A1    Sep. 4, 2008

Related U.S. Application Data

(60) Provisional application No. 60/875,735, filed on Dec. 18, 2006.

(51) Int. Cl.
*A61B 17/50* (2006.01)

(52) U.S. Cl.
USPC .............................................. 606/131

(58) Field of Classification Search
USPC .................. 606/131, 132, 133; 604/289, 290; 451/344, 356, 359; 132/73.6, 76.4
See application file for complete search history.

(56) References Cited

U.S. PATENT DOCUMENTS

| | | | |
|---|---|---|---|
| 5,178,625 A * | 1/1993 | Groshong | 606/159 |
| 6,500,183 B1 * | 12/2002 | Waldron | 606/131 |
| 2005/0022386 A1 * | 2/2005 | Macove | 30/50 |
| 2005/0038448 A1 * | 2/2005 | Chung | 606/131 |
| 2006/0276806 A1 * | 12/2006 | Martinez Zunino | 606/131 |
| 2007/0156124 A1 * | 7/2007 | Ignon et al. | 606/9 |
| 2007/0225732 A1 * | 9/2007 | Cho | 606/131 |

FOREIGN PATENT DOCUMENTS

| | | | | |
|---|---|---|---|---|
| WO | WO 2004103191 A1 * | 12/2004 | | A61B 17/54 |
| WO | WO 2005/109996 | * | 11/2005 | |
| WO | WO 2006/002489 A1 * | 1/2006 | | |

\* cited by examiner

*Primary Examiner* — Ryan Severson
*Assistant Examiner* — Katherine M Shi
(74) *Attorney, Agent, or Firm* — Pearl Cohen Zedek Latzer Baratz LLP

(57) ABSTRACT

A system for treating a skin surface, the system comprising: a base unit comprising: a vacuum source; and a controller; and a treatment device comprising a handle; a treatment head comprising abrading structures with substantially sharp edges for abrading tissue; and a connector to direct negative pressure from the vacuum source to the treatment head.

10 Claims, 9 Drawing Sheets

DERMABRASION DEVICES AND SYSTEMS

CROSS REFERENCE TO RELATED APPLICATION

This application claims the benefit of prior U.S. Provisional Application 60/875,735 filed on Dec. 18, 2006 and entitled Dermabrasion Devices, Systems and Methods, which is incorporated by reference into this application in its entirety.

TECHNICAL FIELD

This application relates to devices and systems related to and useful for dermabrasion.

BACKGROUND

Microdermabrasion is a process that can be used to remove dermal layers and promote the generation of new skin. Microdermabrasion can be performed without anesthetics and generally requires no extended post-treatment recovery period. Accordingly, devices and systems that rapidly and efficiently abrade dermal layers are needed in the skin care industry.

SUMMARY

Provided herein are devices, systems and methods for abrading the dermal and epidermal layers of skin.

In one embodiment, a system for treating the skin surface of a subject is provided. The system includes a base unit comprising a vacuum source, a controller, and a storage compartment. The system further includes a treatment device comprising a treatment handle, a detachable treatment housing, and a treatment bead comprising abrading structures with substantially sharp edges for abrading tissue. The treatment head is associated with the treatment housing, and an internal pipe is connected with the vacuum source.

In another embodiment, a detachable treatment housing having a treatment head is provided. The treatment head includes abrading structures with substantially sharp edges for abrading tissue. The shape of the treatment head is configured to maintain significant contact with a tissue while the treatment head is movably in contact with the tissue. The treatment head can be concave or convex. The shape of the treatment head can be elliptical or non-elliptical. Non-elliptical shapes include circular, triangular or square. In one aspect, the treatment head is movably connected with the treatment housing. The treatment head can be pivotally connected with the treatment housing.

In yet another embodiment, a treatment device is provided. The device includes a treatment handle and a detachable treatment housing distally associated with the treatment handle. The treatment housing includes a treatment head comprising abrading structures with substantially sharp edges for abrading tissue. The treatment housing further includes a cross member connected to the treatment handle and configured to support a filter material. The filter material is positioned between the treatment handle and treatment housing when the handle and housing are operably associated.

Embodiments of the invention may include a system for treating a skin surface of a subject that includes a base unit having a vacuum source, a controller, and a treatment device that may have a handle and a treatment head with sharp edged abrading structures with for abrading tissue. The handle may include a connector to direct negative pressure from the vacuum source to the treatment head.

In some embodiments, the abrading structures may include a diamond material.

In some embodiments, the abrading structures may include a coarse structure.

In some embodiments, the treatment head may be permeable to a pressure exerted by the vacuum source.

In some embodiments, the controller may be programmed to include varying dermabrasion treatment modalities.

In some embodiments, the treatment device may include an aperture to adjust an area through which negative pressure may pass through the treatment head.

In some embodiments, the treatment device may include an adjustment mechanism to change a height of the treatment head relative to a rim of the treatment device.

Some embodiments of the invention include a detachable treatment housing having a treatment head, the treatment head having abrading structures with sharp edges for abrading tissue. The treatment head may be shaped to maintain a relatively constant contact with a tissue while the device is moved along the contours of the surface of a treatment area. The treatment head may be permeable to a negative pressure passing through it.

The details of one or more embodiments of the disclosure are set forth in the accompanying drawings and the description below. Other features, objects, and advantages will be apparent from the description and drawings and from the claims.

BRIEF DESCRIPTION OF DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION

Embodiments described below include dermabrasion systems capable of rapidly and efficiently abrading dermal and epidermal layers of the skin. Such systems incorporate a base unit and a treatment handle operably associated with the base unit, The system includes various components that, in combination, provide unique features for the efficient treatment of skin. Methods of using and manufacturing such systems are also provided.

Figure 1A:
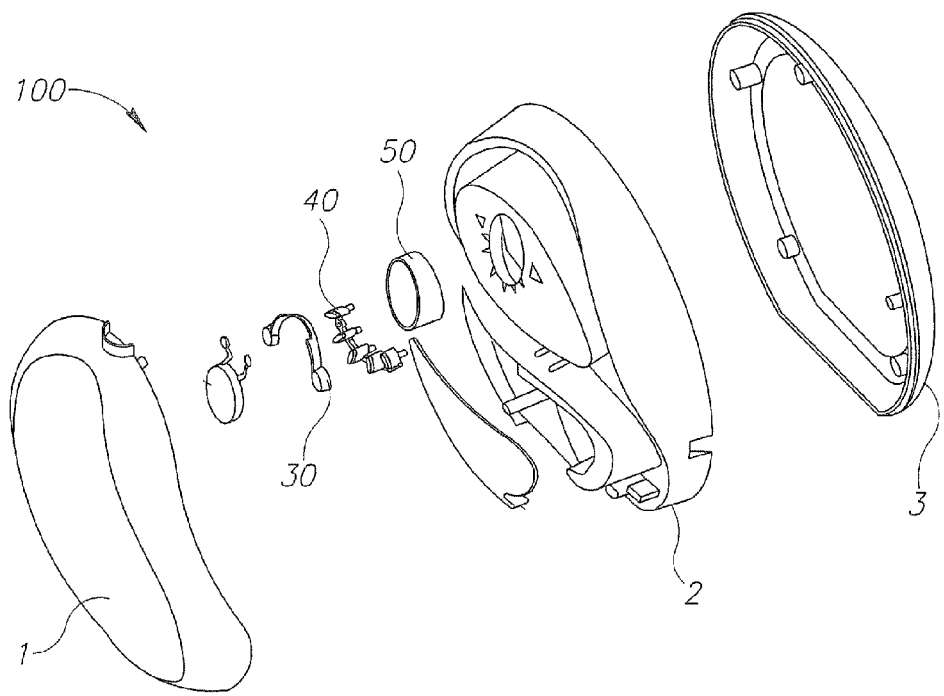
FIG. 1A is a diagram depicting an exploded view of an exemplary base unit of a dermabrasion system, in accordance with an embodiment of the invention.

Referring to FIG. 1A, base unit 100 includes base component 3 comprised of plastic material such as ABS UL94V0 standard material. Base unit 100 optionally includes a vacuum pump and a controller suitable for electronically controlling components of the base unit. Base component 3 of base unit 100 can be comprised of high polish material. The mid component 2 of base unit 100 can be, for example, an ABS UL 94V0 injected plastic part. Base component 3 is connected to mid component 2. In some embodiments, mid component 2 is configured to accommodate treatment device 200 (see FIG. 4) when treatment device 200 is not in use. Cover component is removably connected with mid component 2 at axis 10 (see FIG. 1B). Axis 10 can be, for example, a hinge. Mid component 2 optionally contains a storage compartment for filters. Mid component 2 also optionally contains compartments suitable for accommodating spare treatment heads (see 110 of FIG. 4). For example, such a compartment can include inner lid 1 (see FIG. 1B) as a cover separating the contents of the storage compartment from the other components of the base unit.

In general, components of a system described herein can be composed of plastic injected material. For example, the material can include ABS UL94V0 standard. Components requiring transparency can be made of PC (Polycarbonate) material. Other materials are possible.

Referring again to FIG. 1A, lid 1 may be made of ABS UL94V0 standard injected plastic material with "High-Polish" texture. Lid component 1 is optionally configured to include a mirror assembly 5. Lid component 1 is removably connected to mid component 2. Lid component 1 further optionally includes a product logo.

Referring again to FIG. 1A, mid component 2 may accommodate on/off switch 50, which can be comprised of any suitable material, for example PC (polycarbonate) UL94V0 transparent injected plastic material. On/off switch 50 optionally includes an indicator light to indicate whether the device is on or off. Mid component 2 may be further configured to accommodate operating level guide 40 made of a suitable material such as PC (polycarbonate) UL94V0 Transparent injected plastic material. Operating level guide 40 indicates the operation stage of the system at any moment the system is functioning. Mid component 2 may include level selection switch 30. Level selection switch 30 is a user interface suitable for selecting the level of system function and can be made of any suitable material, such as ABS UL94V0 injected plastic material.

Mid component 2 may include start/stop switch 20 that may control vacuum source. Start/stop switch 20 may be made of any suitable material. Exemplary materials include ABS UL94V0 injected plastic. Start/stop switch 20 may further include a label that indicates whether the switch is in the "on" or "off" position.

Figure 1B:
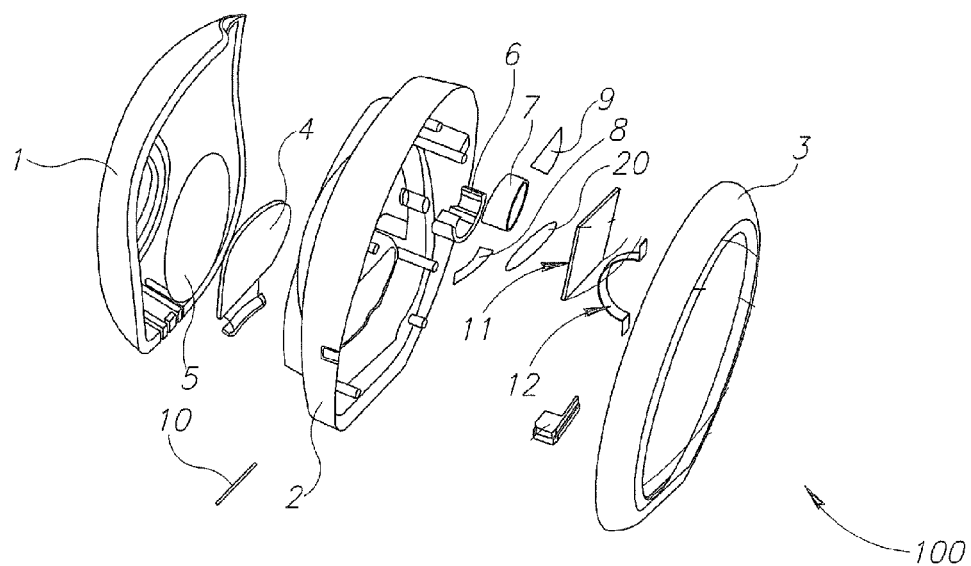
FIG. 1B is a diagram depicting an exploded view of an exemplary base unit of a dermabrasion system, in accordance with an embodiment of the invention.

FIG. 1A and FIG. 1B provide exemplary positions for the components included in mid component 2. It is understood mid component 2 can be designed to accommodate any configuration for the above-described components.

Figure 2:
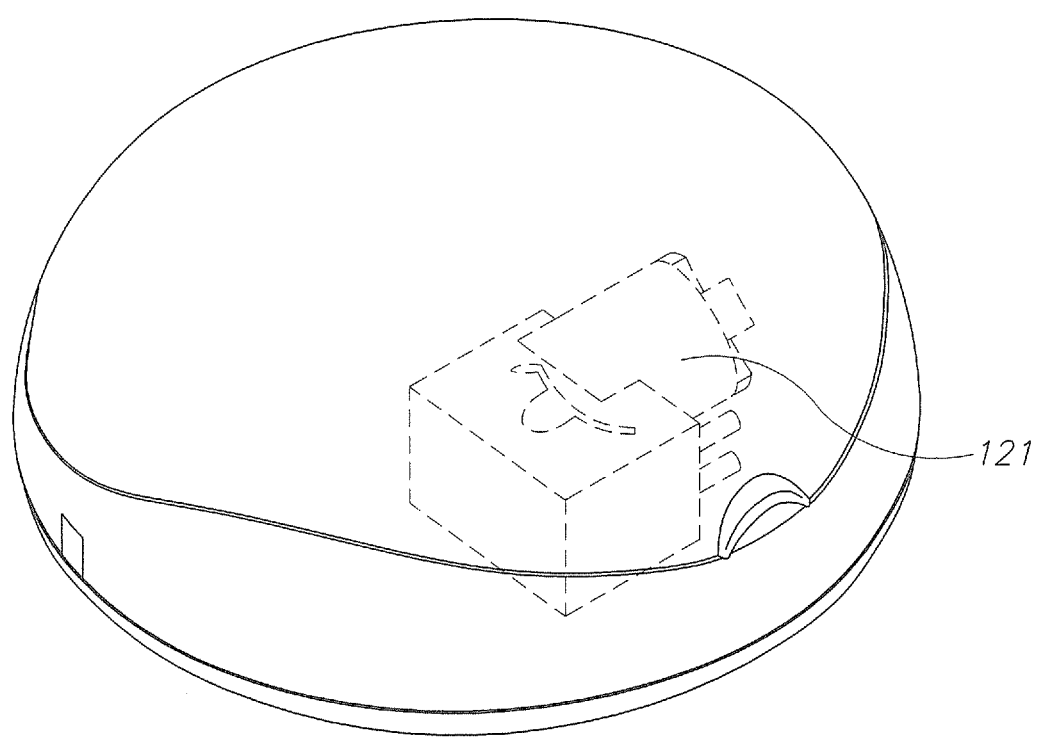
FIG. 2 is a diagram depicting an external view of an exemplary base unit, in accordance with an embodiment of the invention, wherein the base unit is transparent.

Referring to FIG. 1B, intensity light guide 6 is functionally associated with mid component 2 and power light guide 7 and intensity switch 8. Start/stop switch 9 is also associated with mid component 2 and optionally base component 3. Bracket 12 may hold and secure a vacuum source such as a pump 121 as is shown in FIG. 2 below. Controller 11 is functionally associated with any combination of the aforementioned components. Controller 11 optionally includes a storage device for storing information related to dermabrasion treatment modalities. For example, controller 11 can be programmed to perform predetermined treatments suitable for different types of skin and different types of treatment heads (e.g., coarse or fine). The duration of a particular treatment can be controlled such that the user does not exceed the time limit recommended for a particular treatment head. The treatment parameters described above can be implemented in computer programs using standard programming techniques. Such programs are designed to execute on programmable computers each comprising a processor, a data storage system (including memory and/or storage elements).

Figure 3:
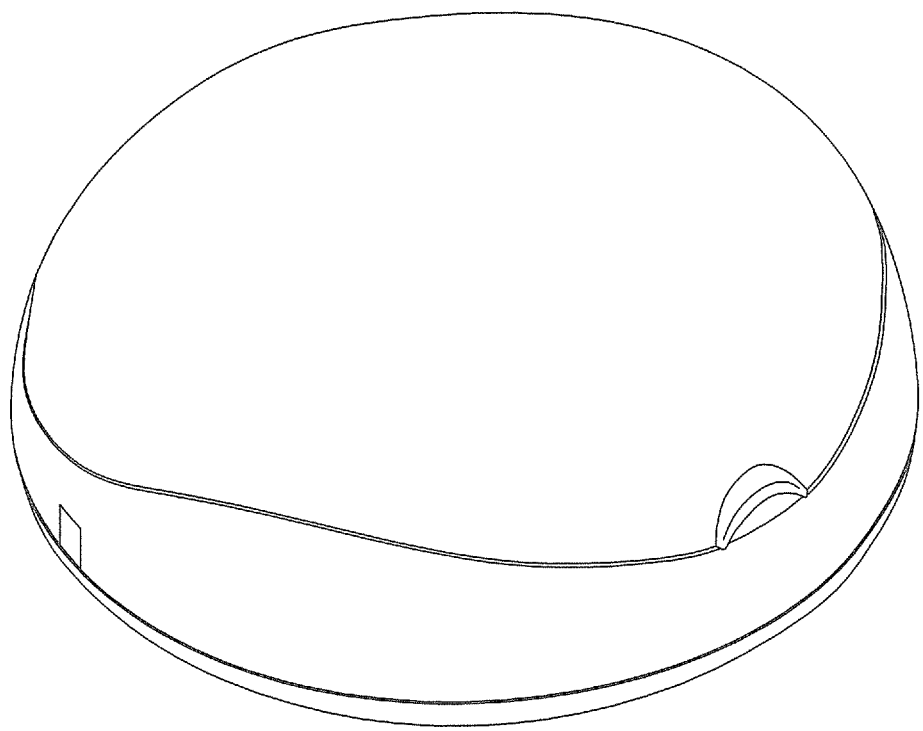
FIG. 3 is a diagram depicting an external view of an exemplary base unit, in accordance with an embodiment of the invention, wherein the base unit is opaque.

Reference is made to FIG. 2, a diagram depicting a transparent view of an exemplary base unit, in accordance with an embodiment of the invention. In some embodiment, vacuum source 121 may be positioned under bracket 12 as appears in FIG. 1B. FIG. 3 shows an external view of the base unit.

Figure 4:
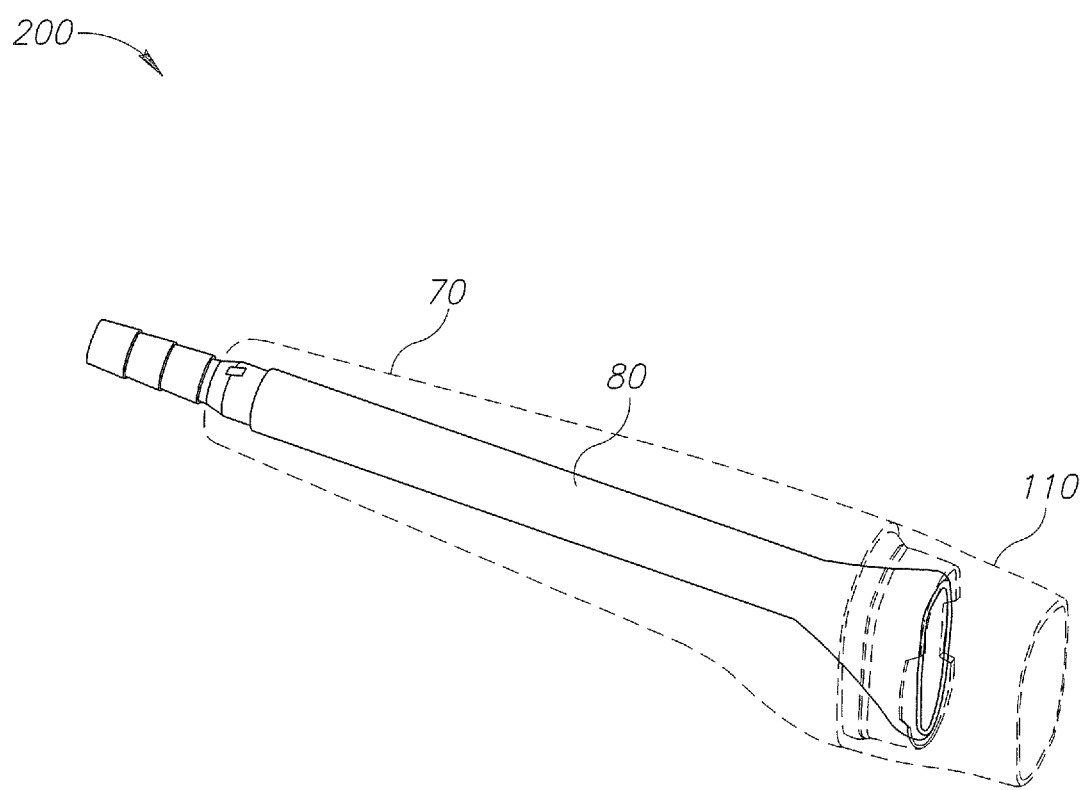
FIG. 4 is a diagram depicting an external view of an exemplary treatment handle of a dermabrasion system, in accordance with an embodiment of the invention, wherein the treatment handle is transparent.
Figure 5:
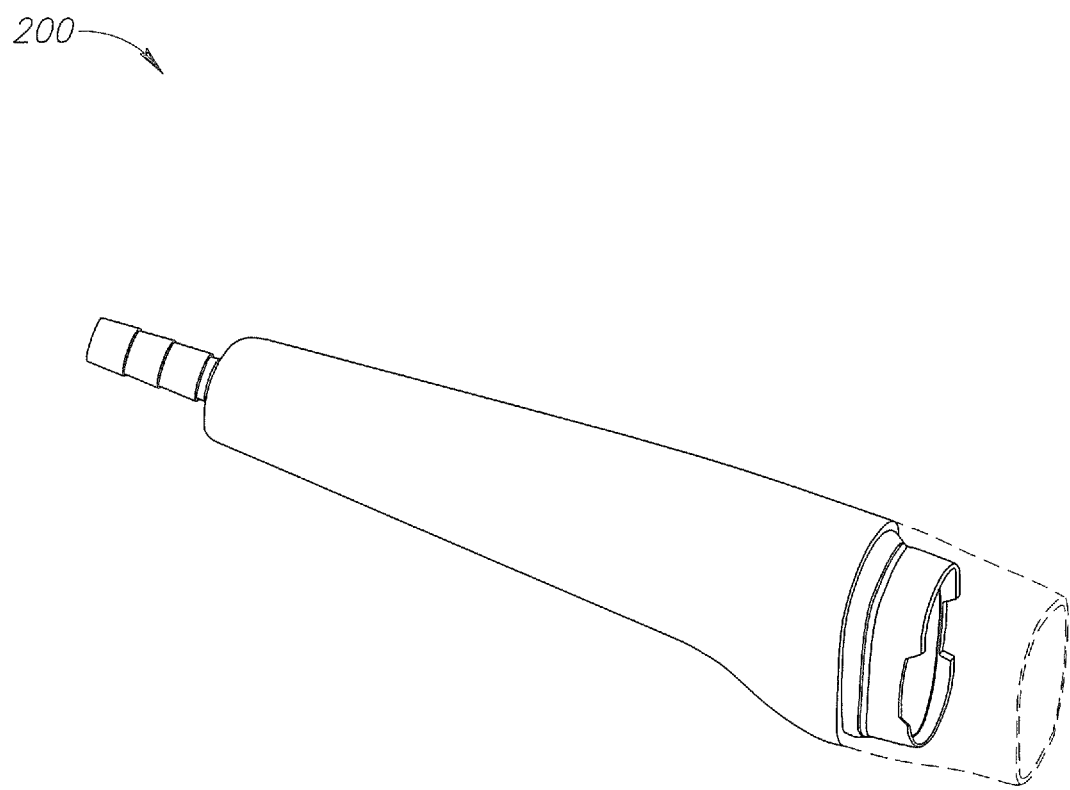
FIG. 5 is a diagram depicting an external view of an exemplary treatment handle, in accordance with an embodiment of the invention, wherein the treatment handle is partially transparent.
Figure 6:
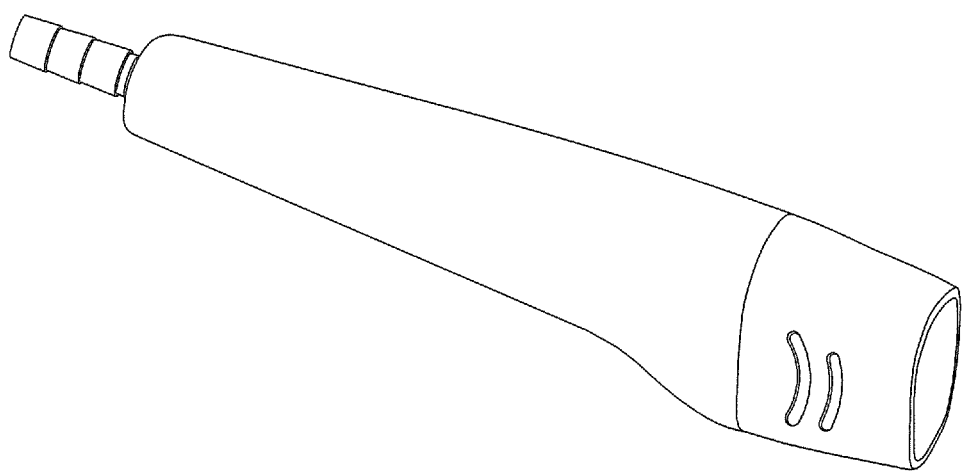
FIG. 6 is a diagram depicting an external view of an exemplary treatment handle, in accordance with an embodiment of the invention, wherein the treatment handle is opaque.
Figure 7:
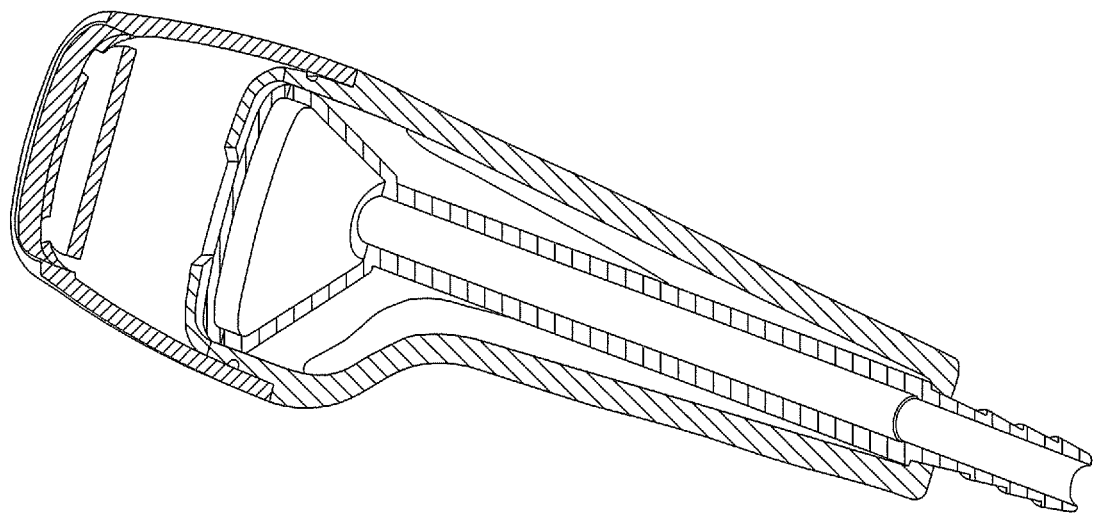
FIG. 7 is a diagram depicting components of an exemplary treatment handle, in accordance with an embodiment of the invention.

FIG. 6 shows an external view of an exemplary treatment handle, wherein the treatment handle is opaque, and FIG. 5 shows the treatment handle, which is shown as partially transparent. Referring to FIG. 4, which shows an external view of the treatment handle of a dermabrasion system wherein the treatment handle is depicted as transparent, treatment device 200 includes handle 70, internal pipe 80, and treatment housing 110. Handle 70 may be made of a suitable material such as ABS UL94V0 injected plastic material. Internal pipe 80 can be comprised of PC (polycarbonate) injected plastic part. Other materials are possible.

Figure 8:
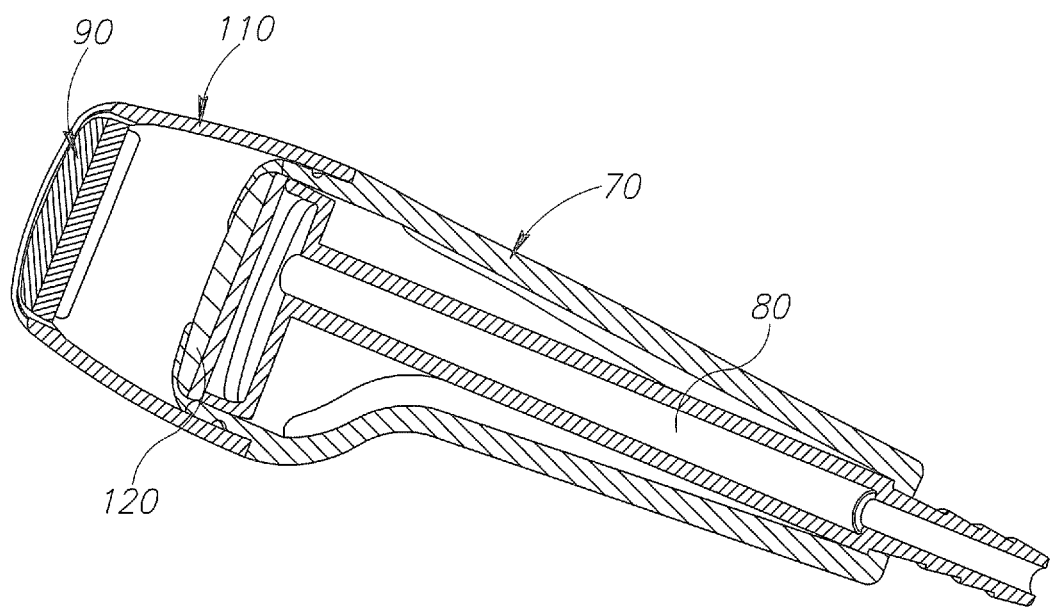
FIG. 8 is a diagram depicting components of an exemplary treatment handle, in accordance with an embodiment of the invention.

Referring to FIG. 8, treatment housing 110 is detachably connected to treatment handle 70 and functionally associated with internal pipe 80. Treatment housing 110 includes treatment head 90 suitably positioned at the distal end of treatment housing so as to effectively contact a skin surface. Housing 110 may be replaceable by, for example, a user when for example head 90 needs to be replaced. Treatment head 90 includes abrading structures with substantially sharp edges for abrading tissue. The abrading structures can be made of any material suitable for abrading skin. For example, treatment head 90 can be made of diamond material, such as diamond powder, with a thickness of about 14 microns. Coarse structures such as aluminum oxide crystals may be used. Referring again to FIG. 8, treatment device 200 can further include filter 120 disposed between treatment head 90 and the distal aperture of pipe 80. Filter 120 may be removable for cleaning or replaceable by a user. In some embodiments, a connector such as a hollow space running through treatment device 200 may be used to direct or channel a negative pressure from a vacuum source to head 90.

Figure 9:
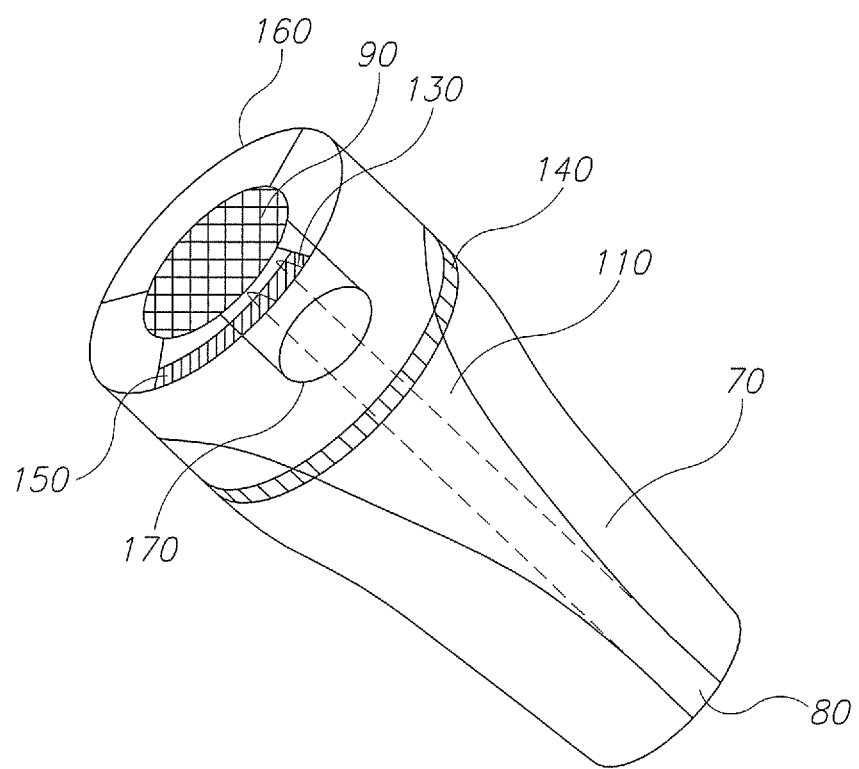
FIG. 9 is a diagram of a treatment handle in accordance with an embodiment of the invention.

Reference is made to FIG. 9, a diagram of a treatment handle in accordance with an embodiment of the invention. In some embodiments, treatment head 90 may be suspended in for example a center of an end of handle 70 by struts 130 or other supports so that a space is provided between an external circumference of head 90 and an inside circumference of handle 70. An adjustable aperture 150 may increase or reduce the amount of negative pressure applied through head 90 by restricting or enlarging the open area between head 90 and the inside of handle 70. Adjustor 140 may permit a user to adjust the restricting or enlarging of the open space between the outer circumference of head 90 and the inner side of handle 70. Varying the negative pressure passing through head 90 or alternatively escaping through the area around the head 90 may adjust the pressure or force exerted by head 90 on an area of skin. In some embodiments, struts 130 may also adjust a height of head 90 relative to an upper rim 160 of handle 70. Such height adjustment may also vary a pressure exerted by head 90 on a skin treatment area. In some embodiments, head 90 may be convex so that a top or distal end of head 90 is higher than sides of head 90. In some embodiments, such as for example, when head 90 is lowered below rim 160, the point of contact between head 90 and a skin treatment area may be reduced, thereby reducing a negative pressure exerted on the skin treatment area as such negative pressure escapes through the lower portions of head 90.

In some embodiments, head 90 may be held by a pivot such as a ball joint 170 so that head 90 may pivot with a contour of a skin treatment area to which it is applied. In some embodiments, ball joint 170 may include a bore or hole to which pipe 80 may be moveably or pivotally attached and through which negative pressure may be channeled to head 90. In some embodiments, head 90 may be attached to a rotating rod that may supply torque to head 90 so that head 90 may spin, vibrate or otherwise move as part of a treatment.

In some embodiments, head 90 may be elliptically or non-elliptically shaped. Non-elliptic shapes may include for example a triangle, square or circular shape. Other shapes are possible.

It is understood that treatment device 200 includes a distal working end that defines a skin interface portion for contacting the skin. The skin interface portion includes treatment housing 110 and treatment head 90. The skin interface portion is in communication with at least one vacuum source for pulling on the skin and for removing tissue from the skin interface.

The skin interface portion optionally includes apertures suitably arranged to deliver treatment media to the skin surface while the treatment device is in operation. Such media include ointments, lotions, and other compounds suitable for treating skin or enhancing the dermabrasion process. The skin interface portion may be porous or semi-porous to such media. The skin interface portion may also be sufficiently porous or permeable to allow the flow through such interface of negative pressure as may be exerted by the internal pipe associated with the treatment device. In some embodiments, negative pressure may be exerted from around the skin interface portion in addition to or instead of by way of through the surface of the skin interface portion.

In practice, the system described above provides for the exfoliation or removal skin surface layers in a controlled manner. After actuation of negative pressure through the internal pipe associated with treatment device, the skin surface is initially drawn into the contact with the treatment head. The operating negative pressures may be in any suitable range that is determined by investigation or as programmed in to the controller. The optimal pressure levels may vary greatly depending on (i) the type of skin targeted for treatment, (ii) the dimensions across the working end, and (iii) the dimensions of the openings associated with the treatment head.

Next, the operator moves the skin interface across a treatment site. The negative pressure within the treatment housing and associated treatment head causes skin debris to be drawn into housing proximate to the skin surface and into the pipe. The sideways or lateral movement of the skin interface causes an abrasion and removal of the skin surface in a controllable manner.

A treatment device described herein is essentially a hand-held instrument that includes a removable treatment housing that defines a skin interface surface portion. Treatment handle mates with treatment housing. A flexible tube extends from treatment handle to a vacuum source associated with base unit. The flexible tube communicates with internal pipe extending through treatment handle. Internal pipe terminates in proximity to the treatment housing associated with the distal end of the treatment device.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. A number of embodiments of the invention have been described. Nevertheless, it will be understood that various modifications may be made without departing from the spirit and scope of the invention. Accordingly, other embodiments are within the scope of the following claims.

I claim:

1. A system for treating a skin surface, the system comprising:
   a base unit comprising:
      a vacuum source; and
      a controller; and
   a treatment device comprising:
      a handle;
      a connector within said handle to direct negative pressure from the vacuum source, said connector terminating with a distal aperture;
      a treatment housing detachable from said handle having an open back end where said treatment housing is connected to said handle and to said distal aperture;
      a treatment head suspended by struts within said housing at a distal end of said housing, comprising abrading structures with substantially sharp edges for abrading tissue, wherein said struts are configured for adjusting a height of said treatment head relative to a rim of said treatment device; and
      a single unpartitioned space internal to said housing and extending between the outer circumference of said treatment head and the inner side of said treatment housing and further extending, between an internal side of said treatment head and said back end of said housing,
      wherein said connector is to direct negative pressure from the vacuum source to said single unpartitioned space through said distal aperture of said connector.

2. The system of claim 1, wherein the abrading structures are comprised of a diamond material.

3. The system of claim 1, wherein the abrading structures are comprised of coarse structures.

4. The system of claim 1, wherein the treatment head is permeable to a pressure exerted by said vacuum source.

5. The system of claim 1, wherein the controller is programmed to include a plurality of dermabrasion treatment modalities.

6. The system as in claim 1, wherein said treatment device comprises an aperture suitable to adjust an area around said treatment head through which negative pressure passes.

7. The system of claim 1, further comprising a filter disposed over said aperture of said connector.

8. A treatment device for treating a skin surface, comprising:
- a treatment handle;
- a connector within said handle to direct negative pressure from a vacuum source connected to said handle, said connector terminating with a distal aperture; and
- a detachable treatment housing distally associated with the treatment handle having an open back end where said treatment housing is connected to said handle and to said distal aperture, wherein, when attached to said handle, said housing comprises a single unpartitioned internal space, and wherein said connector is to direct negative pressure to said single unpartitioned internal space through a distal aperture of said connector, the treatment housing comprising:
- a treatment head suspended by struts at a distal end of said housing, wherein said struts are configured for adjusting a height of said treatment head relative to a rim of said treatment device, wherein said treatment head comprises abrading structures with substantially sharp edges for abrading tissue, wherein said single unpartitioned internal space is between an internal side of said treatment head and said distal aperture of said connector and extending between the outer circumference of said treatment head and the inner side of said treatment housing; and
- a filter disposed over said aperture of said connector.

9. The device as in claim 8, comprising an aperture suitable to adjust an area around said treatment head through which negative pressure passes.

10. The device as in claim 8, wherein said struts are suitable for raising a level of said treatment head above said rim of said treatment device.

\* \* \* \* \*